United States Patent
Dorsch et al.

Patent Number: 5,821,256
Date of Patent: *Oct. 13, 1998

[54] ENDOTHELIN RECEPTOR ANTAGONISTS

[75] Inventors: Dieter Dorsch, Ober-Ramstadt; Mathias Osswald, Zwingenberg; Werner Mederski, Erzhausen; Claudia Wilm, Mühltal; Claus J. Schmitges, Darmstadt; Maria Christadler, Rödermark, all of Germany

[73] Assignee: Merck Patent Gesellschaft mit Beschrankter Haftung, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 698,331

[22] Filed: Aug. 15, 1996

[30] Foreign Application Priority Data

Aug. 16, 1995 [DE] Germany ............ 195 30 032.7

[51] Int. Cl.⁶ ............ C07D 209/48; C07D 209/46; C07D 209/04; A61K 31/34; A61K 31/405; A61K 31/41; A61K 31/42; A61K 31/425

[52] U.S. Cl. ............ 514/359; 514/367; 514/375; 514/379; 514/381; 514/382; 514/387; 514/394; 514/414; 514/416; 514/417; 514/418; 514/419; 548/159; 548/169; 548/171; 548/178; 548/252; 548/217; 548/221; 548/241; 548/259; 548/304.4; 548/306.4; 548/309.7; 548/361.5; 548/454; 548/469; 548/472; 548/475; 548/480; 548/482; 548/483; 548/486; 548/488; 548/491; 548/503

[58] Field of Search ............ 548/454, 469, 548/472, 475, 480, 482, 483, 486, 488, 491, 159, 169, 171, 178, 252, 217, 221, 241, 259, 304.4, 306.4, 309.7, 361.5; 514/414, 416, 417, 359, 367, 375, 379, 387, 394

[56] References Cited

U.S. PATENT DOCUMENTS 5,292,740  3/1994  Burri et al. ............ 514/256

FOREIGN PATENT DOCUMENTS

| | | |
|---|---|---|
| 617 001 | 9/1994 | European Pat. Off. . |
| 63-139149 | 6/1988 | Japan . |
| 93/00879 | 7/1992 | WIPO . |
| 93/08799 | 5/1993 | WIPO . |
| 94/14434 | 7/1994 | WIPO . |
| 96/09818 | 4/1996 | WIPO . |

OTHER PUBLICATIONS

Williams et al., "Pharmacology of L–754,142 . . . " J. of Pharm. and Exp. Ther., vol. 275, No. 3, pp. 1518–1526.

*Primary Examiner*—Mukund J. Shah
*Assistant Examiner*—Deepak Rao
*Attorney, Agent, or Firm*—Millen, White, Zelano & Branigan, P.C.

[57] ABSTRACT

Novel compounds of the formula I

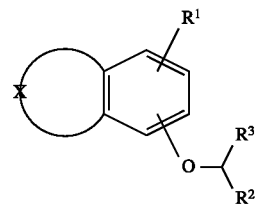

in which
$R^1$, $R^2$, $R^3$ and X have the meaning indicated in claim 1, and their salts exhibit endothelin receptor-antagonistic properties.

18 Claims, No Drawings

ENDOTHELIN RECEPTOR ANTAGONISTS

The invention relates to compounds of the formula I

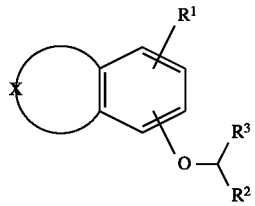

in which

X is a saturated, completely unsaturated or partially unsaturated 3- to 4-membered alkylene chain in which 1 to 3 C atoms can be replaced by N and/or 1 to 2 C atoms can be replaced by 1–2 O and/or 1–2 S atoms, but where at most up to 3 C atoms are replaced and where additionally a mono-, di- or trisubstitution of the alkylene chain and/or of a nitrogen situated therein by A, $R^4$, $R^8$ and/or $NR^4R^{4'}$ can occur, and where furthermore a $CH_2$ group of the alkylene chain can also be replaced by a C=O group, A is alkyl having 1–6 C atoms, in which one or two $CH_2$ groups can be replaced by O or S atoms or by $-CR^4=CR^{4'}-$ groups and also 1–7 H atoms can be replaced by F, $R^1$ is H or A, $R^2$ is $COOR^4$, CN, 1H-tetrazol-5-yl or $CONHSO_2R^8$, $R^3$ is Ar, $R^4$ and $R^{4'}$ in each case independently of one another are H, alkyl having 1 to 6 C atoms or benzyl, Ar is phenyl or naphthyl which is unsubstituted or mono-, di- or trisubstituted by $R^5$, $R^6$ or $R^7$, or a

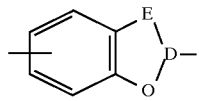

group which is unsubstituted or mono- or disubstituted in the phenyl moiety by $R^5$ or $R^6$, $R^5$, $R^6$ and $R^7$ in each case independently of one another are $R^4$, $OR^4$, Hal, $CF_3$, $OCF_3$, $OCHF_2$, $OCH_2F$, $NO_2$, $NR^4R^{4'}$, $NHCOR^4$, CN, $NHSO_2R^4$, $COOR^4$, $COR^4$, $CONHSO_2R^8$, $O(CH_2)_nR^2$, OPh, $O(CH_2)_nOR^4$ or $S(O)_mR^4$, $R^8$ is phenyl or naphthyl which is unsubstituted or mono-, di- or trisubstituted by A, $OR^1$, $NR^4R^{4'}$ or Hal, E is $CH_2$ or O, D is carbonyl or $[C(R^4R^{4'})]_n$, Hal is F, Cl, Br or I, m is 0, 1 or 2, n is 1 or 2, and their salts.

Similar compounds having indane and indene parent structures are disclosed in WO 93/08799, those with indole systems are disclosed in WO 94/14434, pyrimidine derivatives are disclosed in EP 0 526 708 A1 and phenyl and naphthyl compounds are disclosed in EP 0 617 001 A1.

The invention was based on the object of finding novel compounds having useful properties, in particular those which can be used for the production of medicaments.

It has been found that the compounds of the formula I and their salts have very useful pharmacological properties combined with good tolerability. In particular, they exhibit endothelin receptor-antagonistic properties and can therefore be employed for the treatment of illnesses such as hypertension, cardiac insufficiency, coronary heart disease, renal, cerebral and myocardial ischaemia, renal insufficiency, cerebral infarct, subarachnoid haemorrhage, arteriosclerosis, pulmonary high blood pressure, inflammations, asthma, prostate hyperplasia, endotoxic shock and in complications after the administration of substances such as, for example, cyclosporin, and also other illnesses associated with endothelin activities.

Inter alia, the compounds exhibit a high affinity for the endothelin subreceptors $ET_A$ and $ET_B$. These effects can be determined by customary in vitro or in vivo methods, such as described, for example, by P. D. Stein et al., J. Med. Chem. 37, 1994, 329–331 and E. Ohlstein et al., Proc. Natl. Acad. Sci. USA 91, 1994, 8052–8056.

A suitable method for the determination of the hypotensive effect is described, for example, by M. K. Bazil et al., J. Cardiovasc. Pharmacol. 22, 1993, 897–905 and J. Lange et al., Lab Animal 20, 1991, Appl. Note 1016.

The compounds of the formula I can be employed as pharmaceutically active compounds in human and veterinary medicine, in particular for the prophylaxis and/or therapy of cardiac, circulatory and vascular illnesses, especially of hypertension and cardiac insufficiency.

The invention relates to the compounds of the formula I and their salts and to a process for the preparation of these compounds and their salts, characterized in that (a) a compound of the formula II

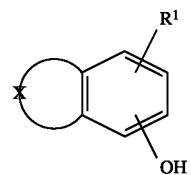

in which $R^1$ and X have the meanings indicated above, is reacted directly or after prior conversion of the hydroxyl group into an anion with a compound of the formula III

in which

Q is Cl, Br, I or a free or reactively functionally modified OH group and $R^2$ and $R^3$ have the meaning indicated above, and/or in that in a compound of the formula I one or more radicals $R^1$, $R^2$ and/or $R^3$ are converted into one or more radicals $R^1$, $R^2$ and/or $R^3$, by i) reducing a nitro group to an amino group, ii) hydrolyzing an ester group to a carboxyl group, iii) converting an amino group into an alkylated amine by reductive amination, iv) converting a carboxyl group into a sulfonamidocarbonyl group and/or converting a base or acid of the formula I into one of its salts.

The meanings of all radicals which occur several times, such as, for example, $R^4$ and $R^8$, are independent of one another.

In the above formulae, A has 1 to 6, preferably 1, 2, 3 or 4 C atoms. A is preferably methyl, furthermore ethyl, propyl, isopropyl, butyl, isobutyl, sec-butyl or tert-butyl, and furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2,- or 1,2,2-trimethylpropyl. E is preferably O, and furthermore $CH_2$ is also preferred.

D is preferably $CH_2$, likewise carbonyl is also referred.

X is preferably —CO—NH—CO—, —CO—NH—$CH_2$—, —NH—CH=CH—, —O—CH=CH—, —N=CH—O—, —N=CH—NH—, —NH—NH—CO—, —NH—N=N—, —NH—CO—$CH_2$—, —NH—CO—O—, —N=CH—S—, —NH—CO—S, —NH—CO—NH—, —O——NH—CO—, —NH—O—CO—, —N=CH—CH=CH—, —CH=N—CH=CH—, —N=N—CH=CH—, —N=CH—N=CH—, —N=CH—CH=N—, —N=N—N=CH—, —NH—CO—CH=CH—, —NH—CH=CH—CO—, —NH—CO—$CH_2$—$CH_2$—, —NH—$CH_2$—$CH_2$—CO—, —NH—CO—N=CH—, —N=CH—NH—CO—, —NH—CO—NH—CO, —NH—CO—NH—$CH_2$—, —CH=N—N=CH—, and furthermore —CH=N—NH—CO—, —CO—NH—NH—CO—, —N=N—NH—CO—, —O—CO—NH—$CH_2$— or —O—CO—NH—CO—.

m is in particular 0, and furthermore preferably also 1 or 2.

n is preferably 1, and furthermore preferably 2.

Hal is preferably F, Cl or Br, but also I.

Ar is unsubstituted, preferably—as indicated—monosubstituted phenyl, in detail preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-hydroxyphenyl, o-, m- or p-nitrophenyl, o-, m- or p-aminophenyl, o-, m- or p-(N-methylamino)phenyl, o-, m- or p-acetamidophenyl, o-, m- or p-(trifluoromethoxy) phenyl, o-, m- or p-cyanophenyl, o-, m- or p-methoxyphenyl, o-, m- or p-ethoxyphenyl, o-, m- or p-carboxyphenyl, o-, m- or p-methoxy-carbonylphenyl, o-, m- or p-ethoxycarbonylphenyl, o-, m- or p-benzyloxycarbonylphenyl, o-, m- or p-(carboxymethyloxy)phenyl, o-, m- or p-(methoxycarbonylmethyloxy)phenyl, o-, m- or p-(methoxycarbonyl-ethyloxy) phenyl, o-, m- or p-(N,N-dimethylamino)phenyl, o-, m- or p-(N-ethylamino)phenyl, o-, m- or p-(N,N-diethylamino) phenyl, o-, m- or p-fluorophenyl, o-, m- or p-bromophenyl, o-, m- or p-chlorophenyl, o-, m- or p-(difluoromethoxy) phenyl, o-, m- or p-(fluoromethoxy)phenyl, o-, m- or p-formylphenyl, o-, m- or p-acetylphenyl, o-, m- or p-propionylphenyl, o-, m- or p-butyrylphenyl, o-, m- or p-pentanoylphenyl, o-, m- or p-(phenylsulfonamidocarbonyl)phenyl, o-, m- or p-phenoxyphenyl, o-, m- or p-methylthiophenyl, o-, m- or p-methylsulfinylphenyl, o-, m- or p-methyl-sulfonylphenyl, o-, m- or p-benzyloxyphenyl, o-, m- or p-cyanomethyloxyphenyl, further preferably 2,3-methylenedioxyphenyl, 3,4-methylenedioxyphenyl, 2,3-ethylenedioxyphenyl, 3,4-ethylenedioxyphenyl, 2,3-(2-oxomethylenedioxy)-phenyl, 2,3-, 2,4-, 2,5-, 2,6-, 3,4- or 3,5-(difluoromethoxy)(carboxymethyloxy)phenyl, 2,3-, 2,4-, 2,5-, 2,6-, 3,4- or 3,5-methoxy-(carboxymethyloxy) phenyl, 2,3-, 2,4-, 2,5-, 2,6-, 3,4- or 3,5-hydroxy-(carboxymethyloxy)phenyl. Ar is further preferably 2,3-dihydrobenzofuranyl, 2,3-dihydro-2-oxofuranyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 3-nitro-4-chlorophenyl, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 3-carboxy-2-methoxy-, 3-carboxy-4-methoxy- or 3-carboxy-5-methoxyphenyl, 2,3,4-, 2,3,5-, 2,3,6-, 2,4,6- or 3,4,5-trichlorophenyl, 2,4,6-tri-tert-butylphenyl, and furthermore preferably 2-nitro-4-(trifluoromethyl)phenyl, 3,5-di-(trifluoromethyl)phenyl, 2,5-dimethylphenyl, 2-hydroxy-3,5-dichlorophenyl, 2-fluoro-5- or 4-fluoro-3-(trifluoromethyl)phenyl, 4-chloro-2- or 4-chloro-3-(trifluoromethyl)-, 2-chloro-4- or 2-chloro-5-(trifluoromethyl)phenyl, 4-bromo-2- or 4-bromo-3-(trifluoromethyl)phenyl, p-iodophenyl, 2-nitro-4-methoxyphenyl, 2,5-dimethoxy-4-nitrophenyl, 3,5-dicarboxyphenyl, 2-chloro-3-nitro-5-carboxyphenyl, 4-chloro-3-carboxyphenyl, 2-methyl-5-nitrophenyl, 2,4-dimethyl-3-nitrophenyl, 3,6- dichloro-4-aminophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methyl-phenyl, 3-bromo-6-methoxyphenyl, 3-chloro-6-methoxy-phenyl, 3-chloro-4-acetamidophenyl, 4-hydroxy-3-carboxyphenyl, 2-methoxy-5-methylphenyl, 2,4,6-tri-isopropylphenyl or naphthyl.

The radical $R^2$ is preferably carbomethoxy, carboethoxy, carbopropoxy, carbobutoxy, carbobenzyloxy, and furthermore cyano, 1H-tetrazol-5-yl or carboxyl, but phenyl sulfonamidocarbonyl or 4-alkylphenylsulfonamidocarbonyl is particularly preferred.

The radical $R^8$ is unsubstituted, preferably—as indicated—monosubstituted phenyl, in detail preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-aminophenyl, o-, m- or p-(N-methylamino)phenyl, o-, m- or p-methoxyphenyl, o-, m- or p-ethoxyphenyl, o-, m- or p-(N,N-dimethyl-amino)phenyl, o-, m- or p-(N-ethylamino) phenyl, o-, m- or p-(N,N-diethylamino)phenyl, o-, m- or p-fluorophenyl, o-, m- or p-bromophenyl, o-, m- or p-chlorophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2-amino-3-chloro-, 2-amino-4-chloro-, 2-amino-5-chloro- or 2-amino-6-chlorophenyl, 2,3,4-, 2,3,5-, 2,3,6-, 2,4,6- or 3,4,5-trichlorophenyl, 2,4,6-tri-tert-butylphenyl, 2,5-dimethylphenyl, 2-hydroxy-3,5-di-chlorophenyl, 3,6-dichloro-4-aminophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 2,4,6-triisopropylphenyl, and furthermore also naphthyl or 5-dimethylamino-1-naphthyl (dansyl).

The compounds of the formula I can have one or more chiral centers and therefore occur in various stereoisomeric forms. The formula I embraces all these forms.

The invention accordingly relates in particular to those compounds of the formula I in which at least one of the radicals mentioned has one of the preferred meanings indicated above. Some preferred groups of compounds can be expressed by the following subformulae Ia to Ig, which correspond to the formula I and in which the radicals not described in greater detail have the meaning indicated in the formula I, but in which in Ia X is —CO—NH—CO—;
in Ib X is —O—CH=N—;
in Ic X is —N=CH—CH=CH—;
in Id X is —NH—CO—S— and
Ar is a

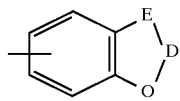

group;
in Ie X is —N=C(A)—N($R^4$)—;
in If X is —N=C(A)—N ($R^4$)— and
Ar is a

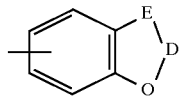

group;
in Ig X is —CO—NH—CO— and
Ar is a

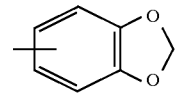

group;
The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart; but in particular in EP 0 617 001 A1), namely under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

Compounds of the formula I can preferably be obtained by reacting compounds of the formula II with compounds of the formula III.

In the compounds of the formula III, Q is preferably Cl, Br, I or a reactively modified OH group such as alkylsulfonyloxy having 1–6 C atoms (preferably methylsulfonyloxy) or arylsulfonyloxy having 6–10 C atoms (preferably phenyl or p-tolylsulfonyloxy).

The reaction is generally carried out in an inert solvent, in the presence of an acid-binding agent, preferably of an alkali metal or alkaline earth metal hydroxide, carbonate or bicarbonate or of another salt of a weak acid of the alkali metals or alkaline earth metals, preferably of potassium, sodium, calcium or cesium. The addition of an organic base such as triethylamine, dimethylaniline, pyridine or quinoline or an excess of the phenol component of the formula II or of the alkylating derivative of the formula III can also be favorable. Depending on the conditions used, the reaction time is preferably from a few minutes to 14 days and the reaction temperature is preferably from approximately 0° C. to 150° C., more preferably from 20° C. to 130° C.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned.

The starting compounds of the formula II are generally known, whereas those of the formula III are generally novel. However, these can be prepared by methods known per se. Thus, for example, methyl benzo[1,3]dioxol-5-ylbromoacetate can be obtained by reaction of methyl benzo[1,3]dioxol-5-yl-hydroxyacetate with phosphorus tribromide. This is expediently carried out at temperatures from about 0° C. to approximately 200° C., preferably from 30° C. and 80° C.

Suitable inert solvents are those already mentioned above.

It is furthermore possible to convert a compound of the formula I into another compound of the formula I by converting one or more radicals $R^1$, $R^2$ and/or $R^3$ into one or more other radicals $R^1$, $R^2$ and/or $R^3$, e.g. by reducing nitro groups (for example by hydrogenation on Raney nickel or Pd-carbon in an inert solvent such as methanol or ethanol) to amino groups and/or hydrolyzing an ester group to a carboxyl group and/or converting an amino group into an alkylated amine by reductive amination and/or converting a carboxyl group into a sulfonamidocarbonyl group.

Free amino groups can furthermore be acylated in a customary manner using an acid chloride or anhydride or alkylated using an unsubstituted or substituted alkyl halide, expediently in an inert solvent such as dichloromethane or THF and/or in the presence of a base such as triethylamine or pyridine at temperatures from about −60° C. to +30° C.

If desired, in a compound of the formula I a functionally modified amino and/or hydroxyl group can be set free by solvolysis or hydrogenolysis according to customary methods. Thus, for example, a compound of the formula I which contains an NHCOR$^4$ or a COOR$^4$ group can be converted into the corresponding compound of the formula I which, instead of this, contains an NH$_2$ or an HOOC group. COOR$^4$ groups can be hydrolyzed, for example, with NaOH or KOH in water, water-THF or water-dioxane at a temperature from about 0° C. to 100° C.

A base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, and furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, e.g. picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts, using bases, (e.g. sodium or potassium hydroxide or carbonate).

The invention furthermore relates to the use of the compounds of the formula I and/or their physiologically acceptable salts for the production of pharmaceutical preparations, in particular by a non-chemical route. In this context, they can be brought into a suitable dose form together with at least one solid, liquid and/or semi-liquid excipient or auxiliary and, if appropriate, in combination with one or more further active compounds.

The invention furthermore relates to pharmaceutical preparations, comprising at least one compound of the formula I and/or one of its physiologically acceptable salts.

These preparations can be used as medicaments in human or veterinary medicine. Possible excipients are organic or inorganic substances which are suitable for enteral (e.g. oral), parenteral or topical administration and do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly. Tablets, pills, coated tablets, capsules, powders, granules, syrups, juices or drops are used, in particular, for oral administration, suppositories for rectal administration, solutions, preferably oily or aqueous solutions, and furthermore suspensions, emulsions or implants for parenteral administration, and ointments, creams or powders for topical application. The novel compounds can also be lyophilized and the lyophilisates obtained used, for example, for the production of injection preparations. The preparations indicated can be sterilized and/or contain auxiliaries such as lubricants, preservatives, stabilizers and/or wetting agents, emulsifiers, salts for affecting the osmotic pressure, buffer substances, colorants, flavorings and/or one or more further active compounds, e.g. one or more vitamins.

The compounds of the formula I and their physiologically acceptable salts can be used in the control of illnesses, in particular of hypertension and cardiac insufficiency.

In this connection, the substances according to the invention are generally preferably administered in doses of from approximately 1 to 500 mg, in particular of from 5 to 100 mg per dose unit. The daily dose is preferably from approximately 0.02 to 10 mg/kg of body weight. The specific dose for each patient, however, depends on all sorts of factors, for example on the efficacy of the specific compound employed, on the age, body weight, general state of health, sex, on the diet, on the time and route of administration, and on the excretion rate, pharmaceutical substance combination and severity of the particular disorder to which the therapy applies. Oral administration is preferred.

Although the compounds belong to a new class of substances, they may be administered, for example, in a manner and in dosages analogous to ACE inhibitors such as captopril or enalapril.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 195 30032.7, filed Aug. 16, 1995 is hereby incorporated by reference.

EXAMPLES

Hereinbefore and hereinafter, all temperatures are indicated in ° C. In the following examples, "customary working up" means: if necessary, water is added, the mixture is adjusted, if necessary, depending on the constitution of the final product, to a pH of between 2 and 10 and extracted with ethyl acetate or dichloromethane, the organic phase is separated off, dried over sodium sulfate and evaporated, and the residue is purified by chromatography on silica gel and/or by crystallization. Rf values on silica gel; eluent: ethyl acetate/methanol 9:1.

Mass spectrometry (MS):
EI (electron impact ionization)
$M^+$
FAB (fast atom bombardment)
$(M+H)^+$ Example 1

To a solution of 1.7 g of 5-hydroxy-1,3-dihydroisoindole-1,3-dione and 4.52 g of 2-(1,3-benzodioxol-5-yl)-2-bromo-N-(4-tert-butylphenylsulfonyl) acetamide in 100 ml of DMF are added 3.3 g of caesium carbonate. The mixture is stirred at room temperature for 2 hours, worked up in the customary manner and 2-(1,3-benzodioxol-5-yl)-2-(1,3-dihydro-1,3-dioxoisoindol-5-yloxy)-N-(4-tert-butylphenylsulfonyl) acetamide, m.p. 215°, is obtained; potassium salt of the compound FAB 575, m.p. 171°.

Analogously, by reaction of methyl benzo[1,3]dioxol-5-ylbromoacetate with 5-hydroxy-1,3-dihydroisoindole-1,3-dione
5-hydroxy-N-methyl-1,3-dihydroisoindole-1,3-dione
5-hydroxy-N-amino-1,3-dihydroisoindole-1,3-dione
5-hydroxy-6-propyl-1,3-dihydroisoindole-1,3-dione
5-hydroxy-1,3-dihydro-1-isoindolone
5-hydroxyindole
6-hydroxy-2-methylbenzoxazole
6-hydroxybenzimidazole
6-hydroxy-2,3-dihydro-1H-indazol-3-one
6-hydroxy-1H-benzotriazole
5-hydroxy-1-methyl-2-propylbenzimidazole
7-hydroxy-6-propylindole
8-hydroxyquinoline
8-hydroxy-7-methylquinoline
8-hydroxy-7-propylquinoline
5-hydroxybenzofuran
4-hydroxy-2-methylindole
5-hydroxy-1,3-benzodioxol,
the methyl 2-(1,3-benzodioxol-5-yl)-2-(T-yloxy) acetates below are obtained,
in which T is 1,3-dihydro-1,3-dioxoisoindole-5, EI 355
N-methyl-1,3-dihydro-1,3-dioxoisoindole-5
N-amino-1,3-dihydro-1,3-dioxoisoindole-5
6-propyl-1,3-dihydro-1,3-dioxoisoindole-5
1,3-dihydro-1-isoindolone-5
indole-5, EI 325
2-methyl-benzoxazole-6 EI 342
benzimidazole-6
2,3-dihydro-1H-indazol-3-one-6
1H-benzotriazole-6
1-methyl-2-propylbenzimidazole-5
6-propylindole-7
quinoline-8, EI 337
7-methylquinoline-8
7-propylquinoline-8
benzofuran-5
2-methylindole-4
1,3-benzodioxol-5.

Example 2

A solution of 1 g of 2-(4-nitrophenyl)-2-(1,3-dihydro-1,3-dioxoisoindol-5-yloxy)-N-(4-tertbutylphenylsulfonyl)acetamide in 25 ml of methanol is hydrogenated to completion at normal pressure and 20° on 1 g of Raney nickel. The mixture is filtered, the solvent is removed and 2-(4-aminophenyl)-2-(1,3-dihydro-1,3-dioxoisoindol-5-yloxy)-N-(4-tert-butylphenylsulfonyl)acetamide is obtained.

Example 3

A solution of 10 g of methyl 2-(1,3-benzodioxol-5-yl)-2-(1,3-dihydro-1,3-dioxoisoindol-5-yloxy)acetate in 300 ml of methanol is treated with 30 ml of 5N sodium hydroxide solution and stirred at room temperature for 3 hours. The mixture is worked up in the customary manner and 2-(1,3-benzodioxol-5-yl)-2-(1,3-dihydro-1,3-dioxoisoindol-5-yloxy)acetic acid, amorphous (softening point 87°), FAB 342, is obtained.

Analogously, by hydrolysis of the methyl 2-(1,3-benzodioxol-5-yl)-2-(T-yloxy)acetates below,
in which T is
N-methyl-1,3-dihydro-1,3-dioxoisoindole-5
N-amino-1,3-dihydro-1,3-dioxoisoindole-5
6-propyl-1,3-dihydro-1,3-dioxoisoindole-5
1,3-dihydro-1-isoindolone-5
indole-5
2-methylbenzoxazole-6
benzimidazole-6
2,3-dihydro-1H-indazol-3-one-6
1H-benzotriazole-6
1-methyl-2-propylbenzimidazole-5
6-propylindole-7
quinoline-8
7-methylquinoline-8
7-propylquinoline-8
benzofuran-5
2-methylindole-4
1,3-benzodioxol-5,
the 2-(1,3-benzodioxol-5-yl)-2-(T-yloxy) acetic acids below are obtained, in which T is
N-methyl-1,3-dihydro-1,3-dioxoisoindole-5
N-amino-1,3-dihydro-1,3-dioxoisoindole-5, FAB 357, m.p. 148°
6-propyl-1,3-dihydro-1,3-dioxoisoindole-5
1,3-dihydro-1-isoindolone-5, m.p. 201°
indole-5, amorphous, FAB 312, m.p. 120°
2-methylbenzoxazole-6, m.p. 174°
benzimidazole-6
2,3-dihydro-1H-indazol-3-one-6
1H-benzotriazole-6
1-methyl-2-propylbenzimidazole-5
6-propylindole-7
quinoline-8, sodium salt, m.p.>300°, FAB 346
7-methylquinoline-8
7-propylquinoline-8, sodium salt, m.p.>300°
benzofuran-5
2-methylindol-4-, m.p. 193°
1,3-benzodioxol-5, m.p. 184°, FAB 317.

Example 4

A solution of 6 g of 2-(4-aminophenyl)-2-(1,3-dihydro-1,3-dioxoisoindol-5-yloxy)-N-(4-tert-butylphenylsulfonyl)acetamide and 0.5 g of titanium tetrachloride in 100 ml of methanol is treated with 1 ml of freshly distilled acetaldehyde. 4 g of sodium cyanoborohydride are then added and the mixture is stirred for 30 hours. Half-concentrated hydrochloric acid is added, the mixture is worked up in the customary manner and 2-(4-ethylaminophenyl)-2-(1,3-dihydro-1,3-dioxo-isoindol-5-yloxy)-N-(4-tert-butylphenylsulfonyl)-acetamide is obtained.

Example 5

A solution of 1 g of 2-(1,3-benzodioxol-5-yl)-2-(1,3-dihydro-1,3-dioxoisoindol-5-yloxy)acetic acid and 0.71 g of carbonyldiimidazole in 100 ml of THF is heated at 60° for 2 hours. 0.93 g of 4-tert-butylbenzenesulfonamide and 0.67 g of 1,8-diaza-bicyclo[5.4.0]-undec-7-ene are then added and the mixture is stirred for a further 1 hour at this temperature. After customary working up, 2-(1,3-benzodioxol-5-yl)-2-(1,3-dihydro-1,3-dioxo-isoindol-5-yloxy)-N-(4-tert-butylphenylsulfonyl)acetamide, m.p. 215°, is obtained.

Analogously, by reaction of 4-tert-butylbenzenesulfonamide with the 2-(1,3-benzodioxol-5-yl)-2-(T-yloxy)acetic acids below,
in which T is
N-methyl-1,3-dihydro-1,3-dioxoisoindole-5
N-amino-1,3-dihydro-1,3-dioxoisoindole-5
6-propyl-1,3-dihydro-1,3-dioxoisoindole-5
1,3-dihydro-1-isoindolone-5
indole-5
2-methylbenzoxazole-6
benzimidazole-6
2,3-dihydro-1H-indazol-3-one-6
1H-benzotriazole-6
1-methyl-2-propylbenzimidazole-5
6-propylindole-7
quinoline-8
7-methylquinoline-8

7-propylquinoline-8
benzofuran-5,
the following 2-(1,3-benzodioxol-5-yl)-2-(T-yloxy)-N-(4-tert-butylphenylsulfonyl)acetamides are obtained, in which T is
- N-methyl-1,3-dihydro-1,3-dioxoisoindole-5
- N-amino-1,3-dihydro-1,3-dioxoisoindole-5
- 6-propyl-1,3-dihydro-1,3-dioxoisoindole-5
- 1,3-dihydro-1-isoindolone-5
- indole-5
- 2-methylbenzoxazole-6
- benzimidazole-6
- 2,3-dihydro-1H-indazol-3-one-6
- 1H-benzotriazole-6
- 1-methyl-2-propylbenzimidazole-5
- 6-propylindole-7
- quinoline-8
- 7-methylquinoline-8
- 7-propylquinoline-8
- benzofuran-5.

Analogously, by reaction of 4-isopropylbenzenesulfonamide with the 2-(1,3-benzodioxol-5-yl)-2-(T-yloxy)acetic acids below, in which T is
- 1,3-dihydro-1,3-dioxoisoindole-5
- N-methyl-1,3-dihydro-1,3-dioxoisoindole-5
- N-amino-1,3-dihydro-1,3-dioxoisoindole-5
- 6-propyl-1,3-dihydro-1,3-dioxoisoindole-5
- 1,3-dihydro-1-isoindolone-5
- indole-5
- 2-methylbenzoxazole-6
- benzimidazole-6
- 2,3-dihydro-1H-indazol-3-one-6
- 1H-benzotriazole-6
- 1-methyl-2-propylbenzimidazole-5
- 6-propylindole-7
- quinoline-8
- 7-methylquinoline-8
- 7-propylquinoline-8
- benzofuran-5
- 1,3-benzodioxol-5, the following 2-(1,3-benzodioxol-5-yl)-2-(T-yloxy)-N-(4-isopropylphenylsulfonyl)acetamides are obtained, in which T is
- 1,3-dihydro-1,3-dioxoisoindole-5, m.p. 159°
- N-methyl-1,3-dihydro-1,3-dioxoisoindole-5
- N-amino-1,3-dihydro-1,3-dioxoisoindole-5
- 6-propyl-1,3-dihydro-1,3-dioxoisoindole-5
- 1,3-dihydro-1-isoindolone-5, FAB 509, m.p.>300°
- indole-5
- 2-methylbenzoxazole-6, FAB 509
- benzimidazole-6
- 2,3-dihydro-1H-indazol-3-one-6
- 1H-benzotriazole-6
- 1-methyl-2-propylbenzimidazole-5
- 6-propylindole-7
- quinoline-8
- 7-methylquinoline-8
- 7-propylquinoline-8
- benzofuran-5
- 1,3-benzodioxol-5, FAB 520.

Example 6

Analogously to Example 1, by reaction of 5-hydroxy-1,3-dihydroisoindole-1,3-dione with the following methyl M-bromoacetates, in which M is
- phenyl
- 1,4-benzodioxan-5-yl
- 1,3-benzodioxol-4-yl
- 2-methoxyphenyl
- 3-methoxyphenyl
- 4-methoxyphenyl
- 2,3-dimethoxyphenyl
- 2,4-dimethoxyphenyl
- 2,5-dimethoxyphenyl
- 3,4-dimethoxyphenyl
- 3,5-dimethoxyphenyl
- 2-carboxymethyloxyphenyl
- 3-carboxymethyloxyphenyl
- 4-carboxymethyloxyphenyl
- 2-difluoromethoxyphenyl
- 3-difluoromethoxyphenyl
- 4-difluoromethoxyphenyl
- 2-methoxy-3-carboxymethyloxyphenyl
- 2-methoxy-4-carboxymethyloxyphenyl
- 2-carboxymethyloxy-3-methoxyphenyl
- 2-carboxymethyloxy-4-methoxyphenyl
- 2-difluoromethoxy-3-carboxymethyloxyphenyl
- 2-difluoromethoxy-4-carboxymethyloxyphenyl
- 2-carboxymethyloxy-3-difluoromethoxyphenyl
- 2-carboxymethyloxy-4-difluoromethoxyphenyl, the following methyl 2-(M)-2-(1,3-dihydro-1,3-dioxoisoindol-5-yloxy)acetates are obtained, in which M is
- phenyl
- 1,4-benzodioxan-5-yl
- 1,3-benzodioxol-4-yl
- 2-methoxyphenyl
- 3-methoxyphenyl
- 4-methoxyphenyl, FAB 342
- 2,3-dimethoxyphenyl
- 2,4-dimethoxyphenyl
- 2,5-dimethoxyphenyl
- 3,4-dimethoxyphenyl
- 3,5-dimethoxyphenyl
- 2-carboxymethyloxyphenyl
- 3-carboxymethyloxyphenyl
- 4-carboxymethyloxyphenyl
- 2-difluoromethoxyphenyl
- 3-difluoromethoxyphenyl
- 4-difluoromethoxyphenyl
- 2-methoxy-3-carboxymethyloxyphenyl
- 2-methoxy-4-carboxymethyloxyphenyl
- 2-carboxymethyloxy-3-methoxyphenyl
- 2-carboxymethyloxy-4-methoxyphenyl 2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl.

Analogously to Example 3, by hydrolysis of the last-mentioned compounds the following 2-(M)-2-(1,3-dihydro-1,3-dioxoisoindol-5-yloxy)acetic acids are obtained, in which M is phenyl
1,4-benzodioxan-5-yl
1,3-benzodioxol-4-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl.

By reaction of the last-mentioned acetic acids with 4-tert-butylbenzenesulfonamide, analogously to Example 5, the 2-(M)-2-(1,3-dihydro-1,3-dioxoisoindol-5-yloxy)-N-(4-tert-butylphenylsulfonyl)acetamides below are obtained, in which M is phenyl
1,4-benzodioxan-5-yl
1,3-benzodioxol-4-yl
2-methoxyphenyl
3-methoxyphenyl
4-methoxyphenyl, m.p. 154°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl.

The following examples relate to pharamaceutical preparations:

Example A: Injection Vials

A solution of 100 g of an active compound of the formula I and 5 g of disodium hydrogen phosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into moulds and allowed to cool. Each suppository contains 20 mg of active compound.

Example C: Solution

A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. The solution is adjusted to pH 6.8, made up to 1 l and sterilized by irradiation. This solution can be used in the form of eyedrops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F: Coated Tablets

Analogously to Example E, tablets are pressed which are then coated in a customary manner with a coating of sucrose, potato starch, talc, tragacanth and colorant.

Example G: Capsules 2 kg of active compound of the formula I are filled into hard gelatin capsules in a customary manner such that each capsule contains 20 mg of the active compound.

Example H: Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula I

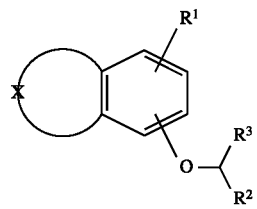

in which

X is —CO—NH—CO—, —CO—NH—CH$_2$—, —NH—CH=CH—, —O—CH=CH—, N=CH—O—, —N=CH—NH—, —NH—NH—CO—, —NH—N=N—, —NH—CO—CH$_2$—, —NH—CO—O—, —N=CH—S—, —NH—CO—S—, —NH—CO—NH—, —O—NH—CO—, or —NH—O—CO, where additionally optionally one to three hydrogen atoms on a carbon and/or a nitrogen atom therein are replaced by A, R$^4$, R$^8$ and/or NR$^4$R$^{4'}$, A is alkyl having 1–6 C atoms, in which one or two CH$_2$ groups is optionally replaced by O or S atoms or by —CR$^4$=CR$^{4'}$— groups and also 1–7 H atoms are optionally replaced by F, R$^1$ is H or A, R$^2$ is CONHSO$_2$R$^8$, R$^3$ is Ar, R$^4$ and R$^{4'}$ in each case independently of one another are H, alkyl having 1 to 6 C atoms or benzyl, Ar is phenyl or naphthyl which is unsubstituted or mono-, di- or trisubstituted by R$^5$, R$^6$ or R$^7$, or a

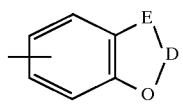

group which is unsubstituted or mono- or disubstituted in the phenyl moiety by R$^5$ or R$^6$, R$^5$, R$^6$ and R$^7$ in each case independently of one another are R$^4$, OR$^4$, Hal, CF$_3$, OCF$_3$, OCHF$_2$, OCH$_2$F, NO$_2$, NR$^4$R$^{4'}$, NHCOR$^4$, CN, NHSO$_2$R$^4$, COOR$^4$, COR$^4$, CONHSO$_2$R$^8$, O(CH$_2$)$_n$R$^2$, OPh, O(CH$_2$)$_n$OR$^4$ or S(O)$_m$ R$^4$, R$^8$ is phenyl or naphthyl which is unsubstituted or mono-, di- or trisubstituted by A, OR$^1$, NR$^4$R$^{4'}$ or Hal, E is CH$_2$ or O, D is carbonyl or (C(R$^4$R$^{4'}$))$_n$, Hal is F, Cl, Br or I, m is 0, 1 or 2, n is 1 or 2, and their salts.

2. A compound of the formula I according to claim 1, which is:

b) 2-(1,3-benzodioxol-5-yl)-2-(1,3-dihydro-1,3-dioxoisoindol-5-yloxy)-N-(4-tert-butylphenylsulfonyl)acetamide;

c) 2-(1,3-benzodioxol-5-yl)-2-(1,3-dihydro-1,3-dioxoisoindol-5-yloxy)-N-(4-isopropylphenylsulfonyl)acetamide.

3. A compound of claim 1, wherein X is —CO—NH—CO—.

4. A compound of claim 1, wherein X is —N=CH—O—.

5. A compound of claim 1, wherein X is —NH—CO—S— and Ar is a

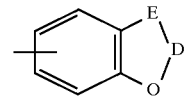

group.

6. A compound of claim 1, wherein X is —CO—NH—CO— and Ar is a

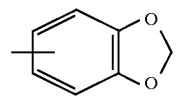

group.

7. A compound of the formula I

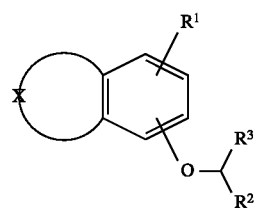

in which

X is —CO—NH—CO—,

A is alkyl having 1–6 C atoms, in which one or two CH$_2$ groups is optionally replaced by O or S atoms or by —CR$^4$=CR$^{4'}$— groups and also 1–7 H atoms are optionally replaced by F, R$^1$ is H or A, R$^2$ is COOR$^4$, CN, 1H-tetrazol-5-yl or CONHSO$_2$R$^8$, R$^3$ is Ar, R$^4$ and R$^{4'}$ in each case independently of one another are H, alkyl having 1 to 6 C atoms or benzyl, Ar is phenyl or naphthyl which is unsubstituted or mono-, di- or trisubstituted by R$^5$, R$^6$ or R$^7$, or a

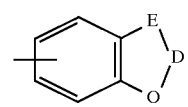

group which is unsubstituted or mono- or disubstituted in the phenyl moiety by R$^5$ or R$^6$, R$^5$, R$^6$ and R$^7$ in each case independently of one another are R$^4$, OR$^4$, Hal, CF$_3$, OCF$_3$, OCHF$_2$, OCH$_2$F, NO$_2$, NR$^4$R$^{4'}$, NHCOR$^4$, CN, NHSO$_2$R$^4$, COOR$^4$, COR$^4$, CONHSO$_2$R$^8$, O(CH$_2$)$_n$R$^2$, OPh, O(CH$_2$)$_n$OR$^4$ or S(O)$_m$ R$^4$, R$^8$ is phenyl or naphthyl which is unsubstituted or mono-, di- or trisubstituted by A, OR$^1$, NR$^4$R$^{4'}$ or Hal, E is CH$_2$ or O, D is carbonyl or [C(R$^4$R$^{4'}$)]$_n$, Hal is F, Cl, Br or I, m is 0, 1 or 2, n is 1 or 2, and their salts.

8. A compound of the formula I according to claim 7, which is:

a) 2-(1,3-benzodioxol-5-yl)-2-(1,3-dihydro-1,3-dioxoisoindol-5-yloxy)acetic acid;
b) 2-(1,3-benzodioxol-5-yl)-2-(1,3-dihydro-1,3-dioxoisoindol-5-yloxy)-N-(4-tert-butylphenylsulfonyl)acetamide; or
c) 2-(1,3-benzodioxol-5-yl)-2-(1,3-dihydro-1,3-dioxoisoindol-5-yloxy)-N-(4-isopropyl-phenylsulfonyl)acetamide.

9. A process for the production of a pharmaceutical composition, comprising bringing a compound of the formula I according to claim 1 and/or one of its physiologically acceptable salts into a suitable dose form together with at least one solid, liquid or semi-liquid excipient or auxiliary.

10. A pharmaceutical composition, containing an endothelin receptor antagonist effective amount of at least one compound of the formula I according to claim 1 or one of its physiologically acceptable salts.

11. A method for inducing an endothelin receptor antagonist effect in a patient which comprises administering to the patient an endothelin receptor antagonist effective amount of at least one compound of the formula I of claim 1 and/or one of its physiologically acceptable salts.

12. The method of claim 11, wherein the compound of the formula I of claim 1 and/or one of its physiologically acceptable salts is administered in a daily dose of from about 0.02 to 10 mg/kg.

13. A method for controlling a disease controllable by endothelin receptor antagonist activity which comprises administering an endothelin receptor antagonist effective amount of at least one compound of the formula I of claim 1 and/or one of its physiologically acceptable salts.

14. The method of claim 13, wherein the compound of the formula I of claim 1 and/or one of its physiologically acceptable salts is administered in a daily dose of from about 0.02 to 10 mg/kg.

15. The method of claim 13, wherein the disease is hypertension; heart failure; coronary heart disease; renal, cerebral or myocardial ischaemia; renal insufficiency; cerebral infarct; subarachnoid hemorrhage; arteriosclerosis; pulmonary hypertension; inflammation; asthma; prostate hyperplasia; endotoxic shock; or complications following administration of cyclosporin.

16. The method of claim 13, wherein the disease is a cardiac, circulatory or vascular disorder.

17. The method of claim 13, wherein the disease is hypertension or heart failure.

18. The method of claim 13, wherein the disease is hypertension and/or cardiac insufficiency.

* * * * *